United States Patent [19]

Moser et al.

[11] Patent Number: 4,679,650

[45] Date of Patent: Jul. 14, 1987

[54] HEARING AID EAR MOLD END PIECE FOR THE AUDITORY CANAL AND HEARING AID EAR MOLD

[75] Inventors: Ludwig M. Moser, Estenfeld; Anton Kammermeier, Welden, both of Fed. Rep. of Germany

[73] Assignee: Westra Electronic GmbH, Fed. Rep. of Germany

[21] Appl. No.: 809,885

[22] PCT Filed: Mar. 28, 1985

[86] PCT No.: PCT/EP85/00132

§ 371 Date: Dec. 5, 1985

§ 102(e) Date: Dec. 5, 1985

[87] PCT Pub. No.: WO85/04779

PCT Pub. Date: Oct. 24, 1985

[30] Foreign Application Priority Data

Apr. 6, 1984 [DE] Fed. Rep. of Germany ....... 3413067

[51] Int. Cl.⁴ ................ A61B 7/02

[52] U.S. Cl. ................ 181/130; 181/135

[58] Field of Search ............... 181/130, 132, 133, 135; 179/107 E

[56] References Cited

U.S. PATENT DOCUMENTS

| | | | |
|---|---|---|---|
| 1,830,198 | 11/1931 | French | 181/135 |
| 2,188,591 | 1/1940 | Carlson | 181/132 X |
| 2,430,229 | 11/1947 | Kelsey | 181/130 X |
| 3,169,600 | 2/1965 | Thomas | 181/135 |
| 3,852,540 | 12/1974 | Dietheim | 179/107 E |
| 3,890,474 | 6/1975 | Glicksberg | 179/107 E |
| 4,532,649 | 7/1985 | Bellafiore | 179/107 E X |

FOREIGN PATENT DOCUMENTS

| | | |
|---|---|---|
| 1270616 | 6/1968 | Fed. Rep. of Germany . |
| 1274657 | 8/1968 | Fed. Rep. of Germany . |
| 2949992 | 7/1980 | Fed. Rep. of Germany . |
| 2050740 | 3/1971 | France . |

*Primary Examiner*—Benjamin R. Fuller
*Attorney, Agent, or Firm*—Weingarten, Schurgin, Gagnebin & Hayes

[57] ABSTRACT

The invention relates to a hearing aid ear mold end piece for the auditory canal, having an outer circumference matching the contours of the auditory canal and a sound discharge opening, whereby end piece (1) is provided on its outer circumference (11) and on the circumference of sound discharge opening (41) with relatively sharp edges (12, 13) projecting in the direction of the inner ear, said end piece being concavely curved in the intermediate end face area (15). The end piece can be made integral with the remainder of the ear mold (3) or as an independent component to be fastened to the remainder of the ear mold.

15 Claims, 3 Drawing Figures

HEARING AID EAR MOLD END PIECE FOR THE AUDITORY CANAL AND HEARING AID EAR MOLD

FIELD OF THE INVENTION

The invention relates to hearing aids, and in particular, to hearing aid ear mold end pieces for use in the auditory canal.

BACKGROUND OF THE INVENTION

The ear mold of a hearing aid is usually cast in plastic after taking an impression of the ear and comprises an outer segment which rests in the outer ear and an adjacent part which is termed the auditory canal olive and projects into the auditory canal, the latter segment extending into the auditory canal for approximately one-third of its length. The auditory canal olive of the ear mold that projects into the auditory canal is provided with a sound channel and serves to conduct the amplified sound generated by the hearing aid into the auditory canal, while simultaneously sealing off the auditory canal from the outside.

In the conventionally employed behind-the-ear hearing aids, the sound channel formed in the ear mold is connected by means of a small plastic tube inserted into this sound channel with the loudspeaker capsule which is located in the hearing aid, in order to conduct the sound generated by the hearing aid from the loudspeaker capsule through the plastic tube into the sound channel of the ear mold and thus into the auditory canal. At the same time, this tube, which is bent into a curve as it passes between the hearing aid and the ear mold, serves to fasten the hearing aid mechanically behind the ear.

One of the problems that arises with hearing aids is the blockage of the outlet opening of the sound channel formed in the ear mold by ear wax. Ear wax has extraordinary creeping ability and therefore readily moves over the dome-shaped convexly curved end face of the ear mold end piece in the auditory canal up to the outlet opening of the sound channel, located approximately at its center, and into the latter as well. This can lead relatively rapidly to blockage of the sound channel in the ear mold, said channel being relatively thin with a conventional diameter in the vicinity of 2 mm. This blockage of the sound channel, which can result in a considerable reduction of the amount of sound coming from the hearintg aid into the auditory canal, cannot be eliminated by cleaning off the ear mold with a handkerchief, which creates the danger that, in attempting to clean it, the blockage can be made even more severe by forcing the ear wax into the sound channel.

Therefore, the goal of the invention is to remedy the problem of blockage by ear wax of the sound outlet opening of the ear mold end piece on the auditory canal side.

SUMMARY OF THE INVENTION

This goal is achieved according to the invention by the special design of the ear mold end piece on the auditory canal side.

The design of the end piece according to the invention makes it possible effectively to prevent blockage of the sound outlet opening by ear wax. The concave curvature of the end piece end face and the sharp edge, especially at the circumference of the sound outlet opening, produce the effect that the ear wax, like a chip produced by a hollow knife, encircles the sharp edge surrounding the sound outlet opening instead of creeping around this edge, as is the case in the conventional convexly curved end segments of ordinary ear molds.

Advantageous improvements and embodiments to the invention are the subject of the subclaims.

Thus, for example, the ear mold end piece according to the invention, like conventional ear molds, can be made integral with the remainder of the ear mold (claim 2) or alternatively, as an independent component to be fastened to the remainder of the ear mold (claim 3). The latter possibility makes it possible on the one hand to make the end piece out of a different material than the remainder of the ear mold and also offers the opportunity of inexpensive mass production of ear mold end pieces, which can then be used in manufacturing individual ear molds after the conventional ear impression of the patient has been taken.

In the case of fabrication of the end piece according to the invention, the latter can be made round or preferably even oval, and, after connection to the remainder of the ear mold manufactured individually by taking an impression of the ear, can be adjusted to the external contours of the auditory canal olive of the remainder of the ear mold by removing material.

A quasi-integral connection of a prefabricated end piece according to the invention with a conventional ear mold to be cast after taking an impression of the ear can be created for example by providing the end piece on the side that faces the remainder of the ear mold with a toothed profile, onto which the remainder of the ear mold is cast, and in this manner a positive connection with the end piece is created (claim 4).

Another possibility for connecting a prefabricated end piece according to the invention with the remainder of the ear mold consists in designing the end piece with a snap-type molded shape by which it can be mounted on a corresponding matching shape on the remainder of the ear mold (claim 5). This molded shape, of course, can be an inner shape that cooperates with an outer shape on the remainder of the ear mold or an outer shape of the end piece that cooperates with an inner shape in the remainder of the ear mold. A design of this type is especially suitable when the end piece is manufactured from a relatively soft material. Then, the end piece can also be readily removed from the remainder of the ear mold, for example for cleaning purposes, and then put back, or if necessary replaced by a new end piece.

Another opportunity for connecting a prefabricated end piece according to the invention with the remainder of the ear mold is the use of a threaded connection (claim 6). A threaded connection can readily be employed when a hard plastic is used. In particular a fine-pitched thread can be used when the end piece is made of Teflon.

Finally, an adhesive connection can be selected for mounting the end piece according to the invention on the remainder of the ar mld (claim 7), whereby the two adhesive surfaces can of course be prepared in advance to produce good adhesion.

Teflon (claim 9) or a soft plastic material such as silicone rubber for example (claim 10) are suitable as materials for the end piece according to the invention, especially if the end piece is prefabricated as a separate component. As already mentioned, the use of Teflon is advantageous when the threaded connection is employed, whereby this material is completely insensitive to ear wax. The use of soft plastic on the other hand is suitable for a snap connection, so that the end piece is then considered a part subject to wear and can be replaced if necessary.

The use of an ear mold end piece designed as a separate component makes the idea of incorporating the loudspeaker capsule into the ear mold attractive. Incorporation of the loudspeaker capsule directly into the ear mold would of course entail considerable acoustic advantages, because the method of transmitting the sound which was formerly conventionally employed, namely from a loudspeaker built into the hearing aid to the sound channel in the ear mold via a thin plastic tube, could be eliminated. Because of the air volume in the loudspeaker capsule built into the hearing aid, the length and diameter of the tube, as well as that of the connected sound channel in the ear mold, coupled with the remaining volume of the auditory canal, which is much wider by comparison with the diameter of the tube, a complex acoustic system is created in which undesirable resonances can occur and whose characteristics are difficult to predict. These problems can be considerably reduced if the loudspeaker capsule can be installed directly in the auditory canal olive of the ear mold, so that the sound then emerges directly into the auditory canal.

Although incorporation of the loudspeaker capsule into the auditory canal olive of the ear mold has already been proposed and already attempted, it has not so far been implemented because of various difficulties. On the one hand there is the problem of the penetration of ear wax into the sound discharge opening, which is much more serious when the loudspeaker capsule is built into the auditory canal olive than when a sound transfer tube is used in the conventional fashion since, when the loudspeaker capsule is built into the auditory canal olive, it can be contaminated and damaged by penetrating ear wax, something which is not the case when the loudspeaker capsule is installed in the hearing aid and a sound transfer tube is employed. Therefore, attempts have already been made to cover the sound discharge opening by a fine screen, but the openings in this screen soon became plugged by ear wax, and this plugging resisted all attempts at cleaning, except by using a solvent.

The ear mold end piece according to the invention makes it possible to solve the problem of contamination by ear wax in this case as well.

Incorporation of the loudspeaker capsule into the auditory canal olive of conventional ear molds, however, faces other problems besides the problem of contamination. One such problem is the connecting wires to the loudspeaker capsule. Since in practice it is impossible to solder the connecting wires of the loudspeaker capsule in the ear mold, which is made of plastic, the connecting wires between the loudspeaker capsule and the hearing aid cannot be replaced and, because of the mechanical stress to which they are exposed, are viewed as parts subject to wear.

The use of an ear mold end piece designed as a separate component according to the invention also provides a solution to the problem. The end piece, designed as an independent component, can be designed as a cover for a loudspeaker chamber formed in the auditory canal olive (claim 8), and if this cover is designed to be removable, in addition to the opportunities already mentioned above, this loudspeaker chamber and consequently a loudspeaker capsule mounted therein will be readily accessible at any time.

In this case, the loudspeaker connecting cable, linking the loudspeaker capsule with the hearing aid, need not be soldered permanently to the loudspeaker capsule, but for example a flat conductor composed of a flexible carrier strip with conductor parts mounted on it, in the manner of printed circuits, can be used, penetrating into the loudspeaker chamber, and the loudspeaker capsule can be provided with contact surfaces which are merely pressed mechanically against the corresponding conductor strips on the flat conductor. The ear mold end piece designed as a cover can serve to generate the contact pressure, said end piece being connected by means of a threaded connection with the remainder of the ear mold and pressing the loudspeaker capsule with its contact areas against the conducting strip when screwed into place. An ear mold with a loudspeaker capsule thus incorporated is the subject of claim 11.

In addition, however, the soldered connection of connecting wires to the loudspeaker capsule is possible, whereby the loudspeaker capsule if necessary can be removed from the loudspeaker chamber after the cover is removed, whereby the soldered connecting wires can simply be pulled out through a feedthrough opening in the auditory canal olive until the connections are exposed.

The incorporation of the loudspeaker capsule into the auditory canal olive of the ear mold, made possible by the invention, is very simple from the manufacturing standpoint since the loudspeaker capsule is not installed in the olive until it is finished. In this way, acoustic testing of various loudspeaker capsules is readily possible.

BRIEF DESCRIPTION OF THE DRAWING

These and further features of the invention will now be described in the detailed description and the accompanying drawing, wherein.

DETAILED DESCRIPTION OF THE INVENTION

Figure 1:
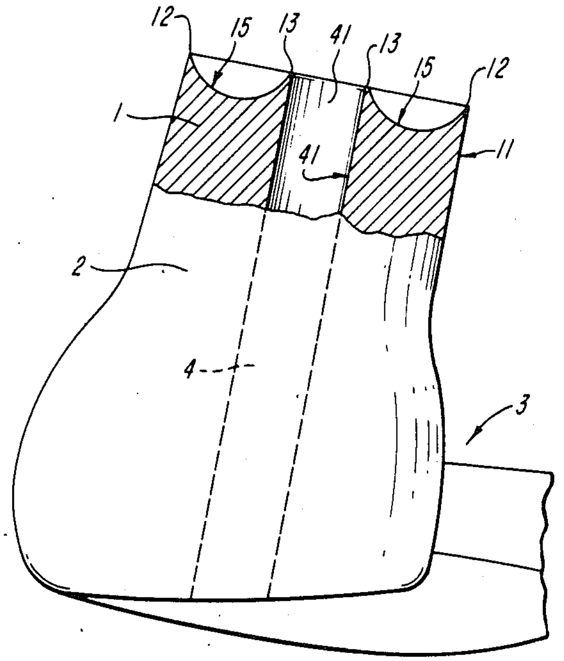
FIG. 1 is a section through an end piece according to the invention, made integral with the remainder of the ear mold.

FIG. 1 shows in lengthwise section the end piece area 1 of auditory canal olive 2 of an ear mold 3. End piece 1 which is designed in one piece with the remainder of the ear mold comprises relatively sharp edges 12 and 13 on its outer circumference 11 and on the circumference of sound discharge opening 41 of sound channel 4 of the ear mold, said edges pointing in the direction of the inner ear. The end face area 15, running between these edges 12 and 13 and pointing in the direction of the inner ear, is concavely curved and forms acute angles with the outer circumference 11 and with the inner wall 42 of sound channel 4.

FIG. 2 shows, once again in lengthwise section, an end piece 1 designed as an independent component, said end piece to be fastened to the remainder of the ear mold. The end face of this end piece, facing the inner ear, is again characterized by relatively sharp edges 12 and 13 projecting at outer circumference 11 and the inner circumference of sound discharge opening 41, as well as a concavely curved end face area 15 between them. On the other side, facing the remainder of the ear mold (not shown), end piece 1 is designed with a snap-type molded shape 16, which serves to mount the end piece on the remainder of the ear mold, the latter being designed with a matching profile into which the molded shape 16 of end piece 1 locks. Molded shape 16 of end piece 1 is shown as an inner profile, which cooperates with an outer profile on the remainder of the ear mold. Of course, this profile arrangement can also be used in reverse.

Figure 2:
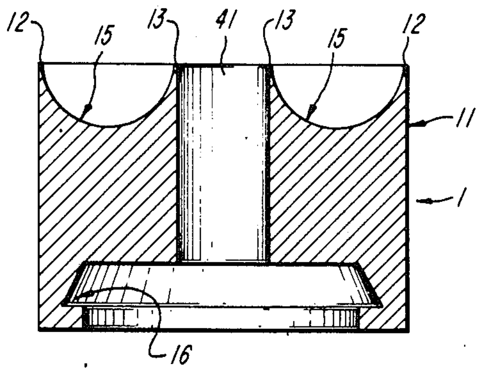
FIG. 2 is an end piece according to the invention designed as a separate component, mountable by means of a snap connection to the remainder of the ear mold.
Figure 3:
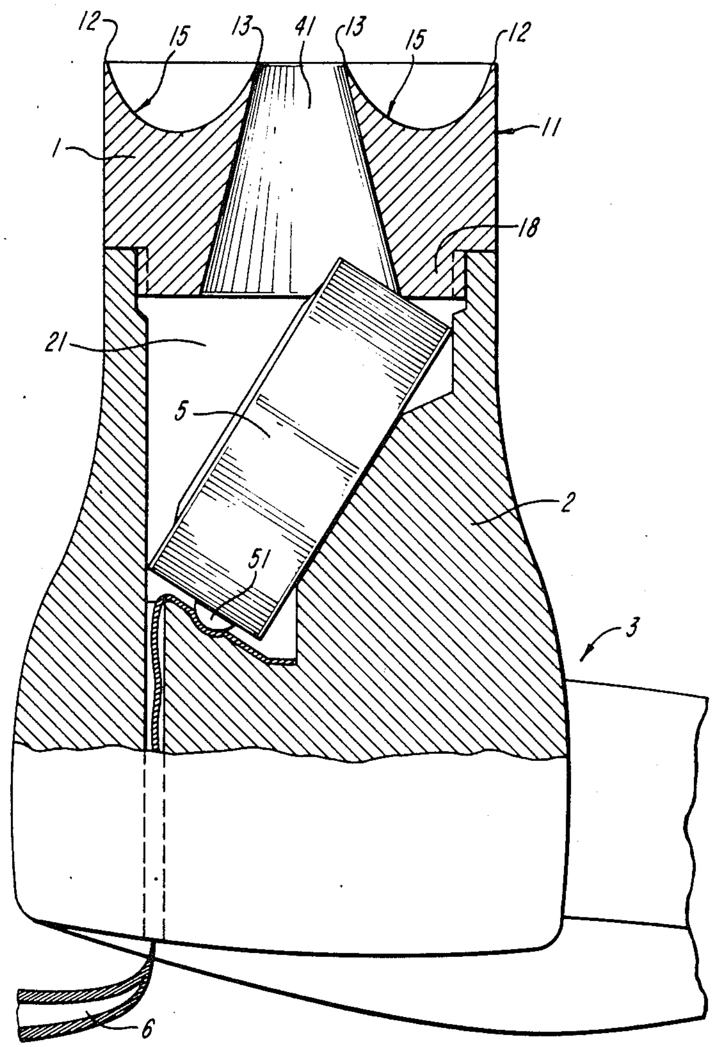
FIG. 3 is a section through the auditory canal olive of an ear mold with loudspeaker capsule built in an end piece screwed on as a cover according to the invention.

FIG. 3 shows, likeewise in lengthwise section, the auditory canal olive part of an ear mold with an end piece 1 mounted coverwise and a loudspeaker capsule 5 mounted in a loudspeaker chamber 21 of olive 2. End piece 1 which, like the end pieces shown in FIGS. 1 and 2 is provided on the auditory canal side on outer circumference 11 and on the circumference of sound discharge opening 41 with projecting sharp edges 12 and 13 in a concavely curved end face area 15 between them, is preferably made of Teflon and has at the end facing the loudspeaker chamber an annular shoulder 18 with an external thread, which is screwed into a matching internal thread on olive 2.

Loudspeaker capsule 5 is mounted loosely in the loudspeaker chamber 21, in which it is held by means of end piece 1 which serves as a cover for the loudspeaker chamber. A flexible flat conductor 6 in the shape of a plastic strip with conducting strips mounted on it serves as the electrical connection to loudspeaker capsule 5. The end of the lead on the loudspeaker side is attached to loudspeaker chamber 21. The loudspeaker capsule is provided with matching contact surfaces 51 by which it contacts the corresponding conducting strips on the flat lead when it is inserted into loudspeaker chamber 21. The required contact pressure is then produced by end piece 1 which serves as the cover the loudspeaker chamber, said end piece, when screwed down onto olive 2, forcing the loudspeaker capsule int the loudspeaker chamber and against the conducting surfaces of the conducting end of flat conductor 6 which is held in place in the loudspeaker chamber.

End piece 1 can therefore be readily unscrewed at any time for servicing, so that the loudspeaker capsule is freely removable and replaceable if required. Likewise, the flat conductor can be replaced readily if needed. Of course it is also possible to connect the loudspeaker capsule to the flat conductor by soldering connecting wires, whereby the loudspeaker capsule can then be removed from the loudspeaker chamber by pulling on the connecting wires, which are movably guided through a corresponding hole in the olive.

What is claimed is:

1. An end piece for use with a hearing aid mold for an auditory canal, the end piece comprising:

a body having an end face and an outer circumference which substantially matches the contours of the auditory canal;

a sound discharge opening passing through said body;

said end face forming a concave annular channel extending at least partially around said sound discharge opening such that a first edge is defined which lies adjacent said outer circumference and a second edge is defined which lies adjacent said sound discharge opening; and said first and second edges being relatively sharp edges.

2. The end piece according to claim 1 including said hearing aid mold, said hearing aid mold including an auditory canal olive having external contours and a sound channel passing therethrough, and wherein said end piece is formed as an integral extension of said auditory canal olive so that said outer circumference is contiguous with said external contours, said sound discharge opening is aligned with said sound channel and said end face is disposed distally from said auditory canal olive.

3. The end piece according to claim 1 wherein said end piece is formed as an independent component having another side in opposed relation to said end face, and wherein said hearing aid mold includes an auditory canal olive having a mating end, external contours and a sound channel passing therethrough, and wherein said end piece is adapted to be fastened to the hearing aid mold by mating said other side with said mating end to have said outer circumference contiguous with said external contours and said sound discharge opening aligned with said sound channel.

4. The end piece according to claim 3 wherein said end piece is provided on the other side with a toothed profile and said mating end is provided with an outer profile complementary to said toothed profile wherein said toothed profile effects a positive connection with said outer profile of the hearing aid mold when the remainder of the mold is cast in place.

5. The end piece according to claim 3 wherein said other side comprises a snap-tape molded shape for mounting on said mating end of the hearing aid mold.

6. The end piece according to claim 3 wherein said other side is provided with a thread and said mating end is provided with a matching thread wherein said end piece is mated to said auditory canal olive by engagement between said thread and said matching thread.

7. The end piece according to claim 3 wherein the other side of the end piece is attached to said mating end of the hearing aid mold by an adhesive connection.

8. The end piece according to claim 3 wherein said auditory canal olive has a loudspeaker chamber formed therein and wherein said end piece comprises a sealing cover for said loudspeaker chamber.

9. The end piece according to claim 1 comprising a Teflon end piece.

10. The end piece according to claim 1 comprising a soft plastic end piece.

11. The end piece according to claim 1, wherein said end piece is removably attached to said hearing aid mold.

12. The end piece according to claim 1, further including a hearing aid mold, comprising:

a body with an exterior, said body having an auditory canal olive with a loudspeaker chamber, said chamber having an open end; and said end piece comprising a cover for sealing the open end of said loudspeaker chamber.

13. The end piece according to claim 12, further comprising:

electrical cable means having a first end with a cable contact surface positioned within said chamber, said cable means extending from said chamber to the exterior of said body;

said loudspeaker chamber adapted to receive a loudspeaker capsule removably inserted therein, said loudspeaker capsule having a capsule contact surface; and said end piece being adapted to urge said loudspeaker capsule against said cable contact surface when the end piece is mounted to said hearing aid mold thereby generating electrical contact between said cable contact surface and said capsule contact surface.

14. A hearing aid mold, comprising:

a body with an exterior, said body having an auditory canal olive with a loudspeaker chamber, said chamber having an open end;

electrical cable means having a first end with a cable contact surface positioned within said chamber, said cable means extending from said chamber to the exterior of said body;

said loudspeaker chamber being adapted to receive a loudspeaker capsule removably inserted therein, said loudspeaker capsulehaving a capsule contact surface; and an end piece including a cover for sealing the open end of said loudspeaker chamber and being adapted to urge said end piece is mounted to said hearing aid mold thereby generating electrical contact between said cable contact surface and said capsule contact surface.

15. The hearing aid mold of claim 14, wherein said end piece includes means for screwing into said ear mold and providing a seal therewith.

* * * * *

UNITED STATES PATENT AND TRADEMARK OFFICE

CERTIFICATE OF CORRECTION

PATENT NO. : 4,679,650

DATED : July 14, 1987

INVENTOR(S) : Ludwig M. Moser; Anton Kammermeier

It is certified that error appears in the above-identified patent and that said Letters Patent is hereby corrected as shown below:

Column 1, line 49, "hearintg" should read --hearing--

Column 2, line 60, "ar mld" should read --ear mold--

Column 5, line 15, "likeewise" should read --likewise-- line 42, "int the" should read --into the--

Column 6, line 33, "snap-tape" should read --snap-type--

Column 8, line 5, "capsulehaving" should read --capsule having-- line 9, "to urge said end piece" should read --to urge said loudspeaker capsule against said cable contact surface when said end piece--

Signed and Sealed this

Twenty-ninth Day of November, 1988

*Attest:*

DONALD J. QUIGG

*Attesting Officer* *Commissioner of Patents and Trademarks*